United States Patent [19]

Marshall et al.

[11] Patent Number: 4,699,139
[45] Date of Patent: Oct. 13, 1987

[54] NASAL CANNULA ASSEMBLY WITH PATIENT COMFORT PAD

[76] Inventors: Marie F. Marshall; Nancy C. Kislow, both of 1330 Berggren Way, Sacramento, Calif. 95815

[21] Appl. No.: 781,717

[22] Filed: Sep. 30, 1985

[51] Int. Cl.⁴ .............................................. A61M 16/00
[52] U.S. Cl. .................................. 128/207.18; 351/122
[58] Field of Search ................... 128/207.18, DIG. 26, 128/207.17, 207.16, 207.15, 207.14; 351/122

[56] References Cited

U.S. PATENT DOCUMENTS

| 619,163 | 2/1899 | Gieberich | 351/122 |
| 2,281,181 | 4/1942 | Clarke | 128/206.13 |
| 2,502,734 | 4/1950 | Lyons | 351/122 |
| 3,993,403 | 11/1976 | Brown | 351/122 |
| 4,333,468 | 6/1982 | Geist | 128/DIG. 26 |
| 4,457,754 | 7/1984 | Buttaravoli | 128/DIG. 26 |
| 4,535,767 | 8/1985 | Tiep et al. | 128/207.18 |
| 4,559,941 | 12/1985 | Timmons et al. | 128/207.18 |

FOREIGN PATENT DOCUMENTS 1579956  8/1969  France ................................ 351/122

Primary Examiner—Henry J. Recla
Attorney, Agent, or Firm—Edgar W. Averill, Jr.

[57] ABSTRACT

An improved nasal cannula assembly having a reduced tendency to cause irritation behind a patient's ears. The improved assembly is of the type having a pair of oxygen supply tubes connected to a cannula affixable into the patient's nostrils. The cannula is held in place by the tubes which are looped over the patient's ears. The portion looped over the ears is covered with a soft pad affixed about the exterior of the supply tubes.

6 Claims, 9 Drawing Figures

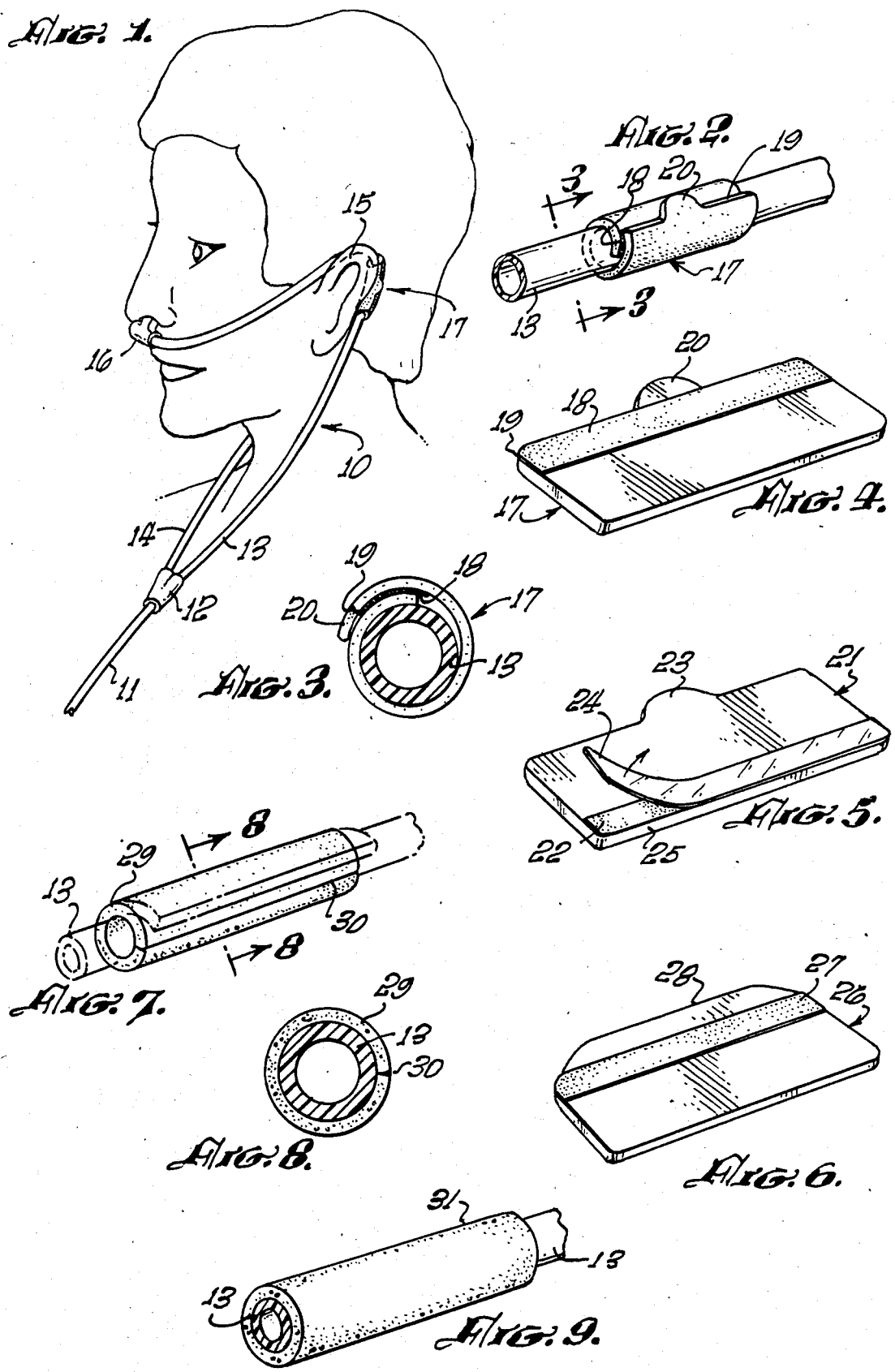

NASAL CANNULA ASSEMBLY WITH PATIENT COMFORT PAD

BACKGROUND OF THE INVENTION

The field of the invention is medical appliances and the invention relates more particularly to nasal cannula assemblies.

Nasal cannula assemblies have found widespread use to provide oxygen or other gasses to a patient frequently over a relatively long period of confinement. Such assemblies have widely replaced oxygen masks and provide much greater comfort than nasal catheters. The use of such devices has proved sufficiently beneficial so that they are widely used not only by respiratory patients, but also for a wide variety of patients who require less energy to breathe with the added oxygen supplied by such assemblies.

Because of the resulting patient benefit, such assemblies are often used over a relatively long period of time and such use can cause irritation and discomfort, particularly above and behind the patient's ears. This discomfort can reach severe proportions and result in sores similar to bed sores which make it very difficult to continue using the assembly. At the present time, the typical solution is to remove the assembly from around the ears and temporarily place it over the patient's head but this, also, causes discomfort at the point where it is supported and, also, can provide additional strain at the location of the cannula.

SUMMARY OF THE INVENTION

It is, thus, an object of the present invention to provide means for improving patient comfort when using a nasal cannula assembly.

The present invention is for an improved nasal cannula assembly to provide improved patient comfort above and behind the patient's ears of the type having a connector affixable to an oxygen supply tube, a pair of oxygen supply tubes leading from the connector to a cannula, affixable into the patient's nostrils and supported by placing the oxygen tubes over the patient's ears. The improvement comprises at least one soft pad affixed to the oxygen supply tube at the point where it is looped about and behind the patient's ears. The pad has a soft, non-irritating exterior surface and has means for being affixed about the desired area of the supply tube. Preferably, the pad has an area of delayed-tack adhesive along one longitudinal edge, and the pad is of sufficient width so that it may be wrapped around the supply tube and, preferably, the adhesive area contacts only the underside of the pad and not the supply tube. Alternatively, the pad may comprise a slit tube which may be placed over the oxygen supply tube at the desired area. Such slit tube is, preferably, made from a sterile, closed cell elastomeric foam.

BRIEF DESCRIPTION OF THE DRAWINGS

FIG. 1 is a perspective view of a patient wearing the improved nasal cannula assembly of the present invention.

FIG. 2 is an enlarged view of a portion of the oxygen supply tube of the nasal cannula assembly shown in FIG. 1, showing that portion of the assembly which is wrapped with a soft pad.

FIG. 3 is a cross-sectional view taken along line 3—3 of FIG. 2.

FIG. 4 is a top perspective view of the pad of the assembly shown in FIG. 1.

FIG. 5 is an alternate embodiment of the pad of FIG. 4.

FIG. 6 is an alternate embodiment of the pad of FIG. 4.

FIG. 7 is an alternate embodiment of a pad useful in the cannula assembly shown in FIG. 1.

FIG. 8 is a cross-sectional view taken along line 8—8 of FIG. 7.

FIG. 9 is a fragmentary, perspective view showing an alternate embodiment of a pad useful in the cannula assembly shown in FIG. 1.

DESCRIPTION OF THE PREFERRED EMBODIMENTS

A nasal cannula assembly is shown in FIG. 1 and indicated generally by reference character 10. The assembly is connected to a main oxygen supply 11 through a connector 12. Two oxygen supply tubes 13 and 14 are looped over the patient's ears 15 and affixed to a cannula 16 which feeds oxygen or other gasses into the patient's nostrils.

As pointed out above, long-term use of the cannula assemblies such as that shown in FIG. 1 can cause irritation behind the patient's ears. The oxygen supply tubes are, typically, fabricated from polyvinyl chloride that has been plasticized to make it flexible. Some patients have a sensitivity to such material and others experience discomfort merely because that portion of the ear lobe is not typically contacted with a foreign object, and the mere presence of the contact can cause irritation.

A soft, generally rectangular pad 17 is shown in perspective view in FIG. 2 wrapped about oxygen supply tube 13. This pad is also shown in FIG. 1 and is placed behind the patient's ear lobe 15. The pad may be fabricated from any soft, sterile substance. It has been found that an elastomeric foam, preferably having closed cells, is very satisfactory for this use. One form of the pad is shown in FIG. 4 where an area of delayed-tack adhesive 18 has been applied along longitudinal edge 19 of pad 17. Also, a tab 20 may be provided to assist in the removal and application of the pad. As shown in FIG. 3, the adhesive 18 does not contact the oxygen supply tube and, thus, the tube is free to move slightly, allowing the pad to remain stationary in place which further eliminates irritation.

The pad of FIG. 5 is identified by reference character 21 and a strip of delayed-tack adhesive 22 is located along longitudinal edge 25. Adhesive 22 is covered by a sheet of treated paper 24 which has been coated with a non-adherent coating such as a silicone coating. Tab 20 of pad 21 is located at the opposite edge from that coated with adhesive and serves the same function of facilitating the removal of the pad if replacement or removal becomes necessary.

Another embodiment of pad is shown in FIG. 6 where pad 26 has a layer of adhesive 27 together with an elongated pull tab 28. The pad may also be formed as a continuous tube which is inserted on the cannula assembly at the time it is being assembled. Such a continuous tube is shown in FIG. 9 where tube 13 is covered by a continuous tube 31 of a closed cell foam.

Instead of providing a flat pad, it is also within the scope of the present invention to provide a slit tube such as that shown in FIG. 7 and indicated by reference character 29. Tube 29 has a slit 30 also shown in FIG. 8 which permits the tube to be opened in the manner shown by the phantom line and placed over the oxygen supply tube as shown in FIG. 8. As above, there is no adhesive which is touching oxygen supply tube 13 and, thus, the tube may tend to stay in place behind the patient's ear lobe rather than move when the supply tube moves.

It has been noted that the use of a thin closed cell foam pad having a thickness of as small as one thirty-second of an inch will still tend to somewhat stiffen the oxygen tubing at the point where the pad is applied. This thickening tends to increase the radius of curvature of the tube and can reduce the irritation caused by the tendency of the tube to closely follow the exterior surface of the ear. By increasing the radius of curvature at this point, less of the tube contacts the outer portion of the ear.

The pads of the cannula assembly of the present invention may be supplied separately from the assembly and used only where some indication of irritation has been observed. The pad can then simply be inserted where most useful for the particular patient, allowing application about any desired portion of the supply tube. The pads may be readily removed and replaced when necessary with resulting enhanced patient comfort.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

What is claimed is:

1. An improved nasal cannula assembly to provide patient comfort above and behind the patient's ears of the type having a connector affixable to an oxygen supply tube, a pair of oxygen supply tubes leading from the connector to a cannula affixable into the patient's nostrils and supported by placing the oxygen supply tubes over the patient's ears wherein the isprovenent comprises:

at least one pad directly adjacent to and surrounding the oxygen supply tube and between the supply tube and the area of maximum irritation at the exterior of the patient's ears, said pad having a soft, non-irritating exterior surface and having means for affixing about the desired area of the oxygen supply tube said pad is rectangular and affixed about the supply tube by an area of delayed-tack adhesive along one longitudinal edge of said rectangular pad, rectangular pad has a sufficient width so that it can be wrapped about the supply tube an amount so that the area of adhesive contacts only opposite longitudinal edge of the pad from that is coated with the adhesive, and wherein said opposite longitudinal edge includes a pull tab extending therefrom.

2. The improved nasal cannula of claim 1 wherein said pull tab extends at the midpoint of said opposite longitudinal edge of the pad.

3. The improved nasal cannula of claim 1 wherein said pad is fabricated from a foamed elastomeric material.

4. The improved nasal cannula of claim 3 wherein said foam is a closed cell foam.

5. The improved nasal cannula assembly of claim 1 wherein said pad has a thickness of between about one thirty-second and one-sixteenth of an inch.

6. The improved nasal cannula of claim 1 wherein said pad completely surrounds the area of maximum irritation at the exterior of the patient's ears.

* * * * *